United States Patent [19]

Redemann

[11] 4,111,938
[45] Sep. 5, 1978

[54] PREPARATION OF 2,3,5-TRICHLOROPYRIDINE

[75] Inventor: Carl T. Redemann, Walnut Creek, Calif.

[73] Assignee: The Dow Chemical Company, Midland, Mich.

[21] Appl. No.: 833,126

[22] Filed: Sep. 14, 1977

[51] Int. Cl.$^2$ .............................................. C07D 213/02
[52] U.S. Cl. ........................... 260/290 HL; 260/290 P
[58] Field of Search ................................. 260/290 HL

[56] References Cited
U.S. PATENT DOCUMENTS 3,993,654  11/1976  Dean et al. .................. 260/290 HL Primary Examiner—Alan L. Rotman
Attorney, Agent, or Firm—S. Preston Jones; C. Kenneth Bjork

[57] ABSTRACT

2,3,5-Trichloropyridine is prepared by the direct reaction of pentachloropyridine or 2,3,5,6-tetrachloropyridine with metallic zinc in the presence of a strongly alkaline aqueous solution and a water-immiscible reaction medium.

3 Claims, No Drawings

PREPARATION OF 2,3,5-TRICHLOROPYRIDINE

BACKGROUND OF THE INVENTION 2,3,5-Trichloropyridine is a well known prior art compound. It is a crystalline material melting at 48°–48.5° C.

2,3,5-Trichloropyridine is useful as an intermediate for preparing various compounds having pesticidal activity. For example, the trichloro compound can be treated with an alkali metal hydroxide employing conventional techniques to prepare 3,5-dichloro-2-pyridinol. The pyridinol can then be reacted with a phosphorochloridate or phosphorochloridothioate to prepare toxicants useful for the control of mite, insect, bacterial and fungal organisms as taught in U.S. Pat. No. 3,244,586.

2,3,5-Trichloropyridine can be prepared by a variety of methods. Sell et al. teach reacting pyridine and phosphorus pentachloride in a sealed tube at 210°–220° C. J. Chem. Soc. 73, 437 (1888). Sell, J. Chem. Soc. 93, 437 (1908) suggest the chlorination of pyridine hydrochloride with chlorine gas at 115°–120° C. for an extended period of time. In a related process, pyridine hydrochloride is treated with liquid chlorine at 80°–225° C. and an HCl pressure of above 30 psig as taught in U.S. Pat. No. 3,732,230. Another method using 2-amino-3,5-dichloropyridine as a starting material is taught in British Pat. No. 1,215,387. Collins et al. J. Chem. Soc. (C), pages 167–174 (1971) teaches the preparation of 2,3,6-trichloropyridine wherein tetrachloro-4-hydrazinopyridine is reacted with cuprous oxide in hot water.

While the above prior art methods are useful in the preparation of 2,3,5-trichloropyridine in small yields on a laboratory scale, these methods are too expensive to be carried out on a commercial scale. Therefore, more practical procedures are continuing to be sought.

SUMMARY OF THE INVENTION

The present invention is directed to a method for preparing 2,3,5-trichloropyridine of high purity and in high yields which comprises reacting 2,3,5,6-tetrachloropyridine or pentachloropyridine with metallic zinc in the presence of a strongly aqueous alkaline solution and a water-immiscible reaction medium.

In carrying out the process of the present invention, the 2,3,5,6-tetrachloropyridine or pentachloropyridine reactant is mixed with the reaction medium and sufficient alkaline reagent to maintain the mixture at a pH of at least 11, preferably 12 to 14 and metallic zinc. The mixture is reacted at a temperature of from about 20° to about 100° C. The reaction is generally complete in from about 1 to about 120 hours. The temperature is usually at the reflux temperature of the mixture. The metallic zinc or alkaline reagent can be added to the mixture either prior to or after the mixture is brought to the reaction temperature. The sequence of addition of the reactants is not critical.

While the zinc reacts to remove chlorine in an equimolar relationship, it is preferred that excess zinc be employed to insure completion of the reaction. The zinc is, therefore, employed in a ratio equivalent to from 1 to 3 gram atoms of zinc per gram atom of chlorine to be removed.

It is important to carry out the reaction in the presence of a strongly alkaline medium with the reaction mixture being at pH of 11–14 since at a lower pH, tetrachloropyridine is more readily reduced to the dichloropyridine reducing the yield of the desired 2,3,5-trichloropyridine.

At the completion of the reaction, the reaction mixture is cooled and with or without dilution with water, filtered to remove any unreacted zinc and other by-products. The filter cake is washed with a solvent such as, for example, toluene or benzene to extract any product adhering thereto. The solvent can, if desired, be added to the reaction mixture before filtration. The solvent is thereafter removed by evaporation leaving the desired product. The product can be further purified, if desired, by fractional distillation or other such conventional techniques.

Representative water-immiscible solvents which can be employed in the present invention include, for example, xylene, toluene, benzene, hexane, heptane, ethyl benzene, anisole and the like.

Representative alkaline reagents for use in the present invention include ethylene/diamine, triethylamine and the hydroxides of ammonium, sodium, potassium, lithium, cesium and rubidium.

SPECIFIC EMBODIMENTS

The following examples illustrate the present invention and the manner by which it can be practiced but, as such, should not be construed as limitations upon the overall scope of the same.

EXAMPLE I — 2,3,5-Trichloropyridine

Into a 5-liter fluted 3-neck flask which was fitted with a reflux condenser, a heater, thermometer and mechanical stirrer was added 251 grams (1.0 mole) of pentachloropyridine, 500 milliliters of toluene and 1.25 liters of 8N sodium hydroxide. The mixture was heated to 90° C., with stirring, and 260 grams (4.0 gram atoms) of zinc dust was added thereto, and the mixture was thereafter refluxed for 2 hours and 45 minutes. The pH of the mixture was 14–15. The reaction mixture was cooled to room temperature and filtered to remove insolubles. The filter cake was washed with toluene and the toluene wash combined with the reaction mixture filtrate. The toluene was removed. Fractional distillation of the mixture through a 15-tray Oldershaw column yielded 126 grams of a colorless liquid boiling at 105°–115° C. at 30 millimeters of mercury which consisted of ~92 percent 2,3,5-trichloropyridine. Recrystallization of the product from hexane, with cooling to −20° C. gave 80 grams of a crystalline product of 99+ percent purity. The product melted at 47°–48° C. and was found upon analysis to have carbon, hydrogen and nitrogen contents of 32.9, 1.2 and 7.8 percent, respectively as compared with the theoretical contents of 32.9, 1.2 and 7.7 percent, respectively, as calculated for the above-named compound.

EXAMPLE II — 2,3,5-Trichloropyridine

To a 500 milliliter, 3-neck flask which was fitted with a reflux condenser, heater, thermometer and stirrer was added 200 milliliters (1.2 moles) of 6N ammonium hydroxide, 39.0 grams (0.60 gram atom) of zinc dust, 100 milliliters of toluene and 25.1 grams (0.1 mole) of pentachloropyridine. The pH of the mixture was 12.6. The mixture was heated to 70° C., with stirring, and held under these conditions for 35 hours. At the end of this period, the reaction mixture was cooled to 20° C. and filtered to remove insolubles. The filter cake was washed with toluene and the toluene combined with the filtrate and concentrated by distillation. Analysis indicated a 2,3,5-trichloropyridine yield of 9.39 grams (52 percent of theoretical).

EXAMPLE III — 2,3,5-Trichloropyridine

To a 500 milliliter, 3-neck flask which was fitted with a reflux condenser, thermometer, stirrer and heater was added 100 milliliters of 1-methoxy-2-propanol, 25.1 grams (0.10 mole) of pentachloropyridine and 39.0 grams (0.60 gram atom) of zinc dust. The flask was heated, with stirring, to 90° C. until all the pentachloropyridine was dissolved. At this time, 100 milliliters of concentrated ammonium hydroxide was added over a 5 hour period. The pH of the mixture was ~12. The mixture was refluxed for 32 hours and the reaction mixture was diluted with two volumes of water and 100 milliliters of toluene. The mixture was filtered to remove insolubles. The toluene was removed by fractionation leaving 30.0 grams of crude 2,3,5-trichloropyridine as an amber-colored oil. Analysis by gas-liquid chromatography showed a yield of 2.1 grams of the desired product (12 percent of theoretical).

raphy indicated a 2,3,5-trichloropyridine content of 140.9 grams (77 percent of theoretical).

EXAMPLE V — 2,3,5-Trichloropyridine

To a 5-liter 3-neck flask fitted with a reflux condenser, a heater, thermometer and a stirrer were added 216.9 grams (1.0 mole) of 2,3,5,6-tetrachloropyridine, 500 milliliters of benzene, 1.0 liter of 8N sodium hydroxide and 130.7 grams (2.0 gram atoms) of zinc dust. The pH of the mixture was 14–15 and the mixture was heated and refluxed, with stirring, for 7 hours. After completion of the reaction, the reaction mixture was cooled and filtered. The filter cake was washed with benzene and the benzene wash was combined with the filtrate. Gas-liquid chromatography of the mixture indicated a 2,3,5-trichloropyridine content of about 131.35 grams (72 percent of theoretical).

By following the above procedures, additional runs showed similar yields of the 2,3,5-trichloropyridine product. Such additional runs are set forth below in Table I.

TABLE I

| Reflux Temperature in ° C | Moles of Pentachloropyridine Starting Material | Mole Ratio of Zinc to Pentachloropyridine | Reaction Time in Hours For Maximum Yield | Base And Strength | pH of Reaction Mixture | Mole Ratio of Base to Pentachloropyridine | Solvent Employed | Yield of 2,3,5-Trichloropyridine in Grams | Yield of 2,3,5-Trichloropyridine in Percent |
|---|---|---|---|---|---|---|---|---|---|
| 50° C | 0.10 | 3:1 | 23 | 18N NH$_4$OH | 13 | 9:1 | isopropanol | 9.12 | 50 |
| 70° C | 0.10 | 6:1 | 35 | 6N NH$_4$OH | 12.6 | 12:1 | toluene | 11.49 | 63 |
| 90° C | 0.10 | 6:1 | 32 | 18N NH$_4$OH | 12 | 18:1 | 2-methoxy-1-propanol | 2.19 | 12 |
| 70° C | 0.10 | 6:1 | 17 | 6N NaOH | 14–15 | 12:1 | toluene | 10.76 | 59 |
| 90° C | 0.10 | 3:1 | 3.8 | 6N NaOH | 14–15 | 12:1 | toluene | 11.86 | 65 |
| 90° C | 0.10 | 4.5:1 | 25 | 6N NaOH | 14–15 | 6:1 | toluene | 8.03 | ~44 |
| 90° C | 0.10 | 4.5:1 | 4 | 6N NaOH | 14–15 | 9:1 | toluene | 9.85 | 54 |
| 90° C | 0.10 | 4.5:1 | 3 | 8N NaOH | 14–15 | 9:1 | toluene | 12.04 | 66 |
| 23° C | 0.10 | 4.5:1 | 114 | 8N NaOH | 14–15 | 9:1 | toluene | 4.56 | ~25 |
| 96° C | 0.10 | 4.5:1 | 5 | 10N NaOH | 14–15 | 9:1 | toluene | 11.31 | 62 |

EXAMPLE IV — 2,3,5-Trichloropyridine

Into a 5-liter fluted 3-neck flask fitted with a reflux condenser, a heater, thermometer and a stirrer was added 251.0 grams (1.0 mole) of pentachloropyridine, 500 milliliters of benzene and 1.25 liters of 8N sodium hydroxide (10 moles). The mixture was heated to ~75° C., with stirring. At this time, 260.0 grams (4.0 gram atoms) of zinc dust was added and the mixture refluxed at ~79° C. for a total reaction time of 5 hours. The pH of the reaction mixture was 14–15. At the completion of the reaction, the reaction mixture was cooled to room temperature and filtered to remove insolubles. The filter cake was washed with benzene and the benzene wash was combined with the filtrate. Gas-liquid chromatog-

What is claimed is:

1. A method for preparing 2,3,5-trichloropyridine which comprises reacting at a pH of 11 or above and at a temperature of from about 20° to about 100° C., a pyridine reactant selected from the group consisting of 2,3,5,6-tetrachloropyridine and pentachloropyridine with from 1 to 3 gram atoms of zinc per gram atom of chlorine to be removed, in the presence of an alkaline reagent and a water-immiscible reaction medium.

2. The method as claimed in claim 1 wherein 2,3,5,6-tetrachloropyridine is the pyridine reactant.

3. The method as claimed in claim 1 wherein pentachloropyridine is the pyridine reactant.

* * * * *